US012023351B2

(12) United States Patent
Liu et al.

(10) Patent No.: US 12,023,351 B2
(45) Date of Patent: Jul. 2, 2024

(54) MODIFIED NANO-SILICA GEL FOR IMPROVING SYMPTOMS CAUSED BY BACTERIA AND VIRUSES AND PREPARATION METHOD AND APPLICATION THEREOF

(71) Applicant: HOU CHI CHEMICAL CO., LTD., Taipei (TW)

(72) Inventors: Te-Hsin Liu, Taipei (TW); Wei-Lung Yu, Taichung (TW)

(73) Assignee: Hou Chi Chemical Co., Ltd., Taipei (TW)

( * ) Notice: Subject to any disclaimer, the term of this patent is extended or adjusted under 35 U.S.C. 154(b) by 134 days.

(21) Appl. No.: 17/648,302

(22) Filed: Jan. 19, 2022

(65) Prior Publication Data

US 2023/0226104 A1  Jul. 20, 2023

(51) Int. Cl.
*A61K 33/00* (2006.01)
*A61K 9/00* (2006.01)
*A61K 9/06* (2006.01)
*A61P 31/14* (2006.01)
*B82Y 40/00* (2011.01)
*B82Y 5/00* (2011.01)

(52) U.S. Cl.
CPC ............ *A61K 33/00* (2013.01); *A61K 9/0053* (2013.01); *A61K 9/06* (2013.01); *A61P 31/14* (2018.01); *B82Y 5/00* (2013.01); *B82Y 40/00* (2013.01)

(58) Field of Classification Search
CPC ........ A61K 33/00; A61K 9/0053; A61K 9/06; A61P 31/14; B82Y 5/00; B82Y 40/00
See application file for complete search history.

(56) References Cited

FOREIGN PATENT DOCUMENTS

TW     I701216 B     8/2020

OTHER PUBLICATIONS

Le, et al., "Synthesis of silica nanoparticles from Vietnamese rice husk by sol-gel method", 2013, Nanoscale Research Letters, 8:58 (Year: 2013).*
Rafiee et al., "Optimization of synthesis and characterization of nanosilica produced from rice husk (a common waste material)", 2012, International Nano Letters, 2:29 (Year: 2012).*

(Continued)

*Primary Examiner* — Bethany P Barham
*Assistant Examiner* — Ayaan A Alam
(74) *Attorney, Agent, or Firm* — Wang Law Firm, Inc.

(57) ABSTRACT

A modified nano-silica gel for improving symptoms caused by bacteria and viruses and a preparation method and an application thereof. The patented nano-silica gel is modified by a modified compound to obtain a modified nano-silica gel to effectively reduce an amount of toxins excreted by sows, thereby providing piglets with a safe environment that is more suitable for survival. The modified nano-silica gel of the invention comprises: a nano-silica gel with a content of 13.0-92.3 wt %; a modified compound with a content of 0.15-3.50 wt %, the modified compound is an organic compound, a weight ratio of the nano-silica gel to the modified compound is 620:1 to 3.5:1; and water with a formula of $H_2O$ and a content of 7.5-86.8 wt %; the nano-silica gel, the modified compound and the water are stirred and mixed at a temperature of 40-80° C. to prepare the modified nano-silica gel.

2 Claims, 2 Drawing Sheets (56) References Cited

OTHER PUBLICATIONS

Acme Hardesty, Lauric Acid, 2014, screenshot of Wayback machine; from https://web.archive.org/web/20140616064436/https://www.acme-hardesty.com/product/lauric-acid-c12/ (Year: 2014).*

Zuwanna, The impact of solvent concentration on the characteristic of silica from rice husk ash using sol gel method, 2021, IOP Conf. Ser.: Mater. Sci. Eng. 1087 012060, 1-7 (Year: 2021).*

\* cited by examiner

MODIFIED NANO-SILICA GEL FOR IMPROVING SYMPTOMS CAUSED BY BACTERIA AND VIRUSES AND PREPARATION METHOD AND APPLICATION THEREOF

BACKGROUND OF THE INVENTION

Field of Invention

The invention relates to a nano-silica gel and a preparation method thereof, and more particularly to a modified nano-silica gel and a preparation method and an application thereof for improving symptoms caused by bacteria and viruses.

Description of Related Art

Porcine epidemic diarrhea virus (PEDV, also known as PED virus) can cause acute diarrhea, vomiting, dehydration in piglets (suckling piglets), and high mortality diseases in newborn piglets younger than 2 weeks old, causing serious economic loss in the pig industry. Although many PEDV vaccines have been developed and used on-site abroad, since Taiwan does not currently have effective and legal PEDV vaccines available, many farms can only use feedback to treat or prevent PED virus infection. The advantages of the method can stimulate the mucosa of the digestive tract of the sow and quickly produce an immunoreaction, so that the piglet can be protected from the PED virus infection by maternally-derived antibody IgA obtained from colostrum and milk within a few days after birth; however, there is a great risk of causing the spread of other pathogens (such as: porcine circovirus type II, porcine reproductive and respiratory syndromes, salmonella, etc.). Therefore, when there is no effective and adequate vaccine available, it is extremely important to find a way to replace feedback.

It is worth noting that the nano-silica gel is a modified nano-silica gel compound through excellent surface modification to enhance the attraction of its negative charge, which makes it particularly capable of attracting and binding with the positive charge of basic amino acids on the surface of the virus. The anti-virus mechanisms of the nano-silica gel are as follows: firstly, after the nano-silica gel is combined with the virus, it blocks the virus from contacting the cell, making it unable to bind to the receptor of the cell; and secondly, the nano-silica gel interferes with the transcription of the virus and prevents the release of virus particles produced by the infected host cell, thus preventing the replication and spread of the virus.

Therefore, the applicant of the invention proposed a patent "nano-silica gel and antibacterial and antiviral applications thereof" with publication number I701216. The nano-silica gel disclosed in this patent comprises: a silica, which is an inorganic clay with a content of 0.9~4.7%; a delamination agent, which is a polysaccharide, composed of a plurality of glucosamines (deacetylated units) and a plurality of N-acetyl glucosamines, and combined through β-(1-4) glycosidic bonds, a content of the delamination agent is 0.6~3.4%; an acid, which is an acidic compound with a content of 0.3~2%; and water with a formula of $H_2O$, and a content of 92~98%; wherein, a particle size of the nano-silica gel is less than 500 nm.

Accordingly, the patented nano-silica gel achieves an antibacterial effect based on the following antibacterial mechanisms: (1) the charge on the nano-silica gel will attract the polarity of the cell wall surface of bacteria and pathogens, after attaching on the surface, ion exchange and oxidation are used to shrink and damage the cell wall, thereby disintegrating the bacteria; (2) after the surface of the bacterial cell wall is attracted and attached by the nano-silica gel, the position of bacterial respiration and the function of quorum sensing will be shielded, making it impossible for the bacteria to communicate with each other and lose their activity; and (3) physical attach to the surface of the bacteria causes the bacteria to lose their mobility, overlap together and lose their ability to function, such as making the flagella of *Salmonella* to interlace and unable to move. The patent achieves the provision of the nano-silica gel with antibacterial and antiviral effects through the aforementioned technical solutions, and experiments have confirmed that the nano-silica gel has the ability to reduce the viral activity of the PED virus. In addition, it has been proved to be effective in reducing the amount of viruses in pig breeding farms in vivo experiments. After the sows are administered with the nano-silica gel two weeks before delivery or after delivery, the amount of PED viruses in the fecal samples of the sows decreases, and the amount of PED viruses in the feces of the piglets also drops.

However, from the experimental data of the patent, it can be known that administration of the patented nano-silica gel did not effectively improve the symptoms of diarrhea in the piglets, and the mortality rate of the piglets within one week of age was still as high as 100%; and after the sows were administered with the nano-silica gel two weeks before delivery, although the piglet survival rate reached 86%, there were still piglets with diarrhea sporadically. After analysis, it was found that in the pasture environment that had experienced repeated PED epidemics and where epidemic control was carried out through feedback, due to the biosecurity and feedback in the pasture might be improperly operated, PEDV was still opportunistically infecting the sows and piglets in the pasture environment. Some sows were protected from PED virus infection, especially those with production of antibodies in their bodies after being infected with PED virus. Although the test results of PED virus in the feces of the sows were mostly negative or the amount of viruses was extremely low, the piglets continued to consume maternally-derived antibodies due to the presence of PED virus in the environment and were eventually infected with PED virus.

Therefore, how to prepare an antibacterial and antiviral nano-silica gel that is not environmentally toxic and capable of effectively reducing an amount of toxins excreted by sows is a technical issue to be solved by the invention.

SUMMARY OF THE INVENTION

In order to overcome the above technical problems, the invention provides a modified nano-silica gel for improving symptoms caused by bacteria and viruses and a preparation method and an application thereof, the patented nano-silica gel is modified by a modified compound selected from alcohol, acid, and ester compounds with carbon numbers of 8 to 18 to obtain a modified nano-silica gel to effectively reduce an amount of toxins excreted by sows, thereby providing piglets with a safe environment that is more suitable for survival.

A first object of the invention is to provide a modified nano-silica gel comprising: a nano-silica gel with a content of 13.0-92.3 wt %; a modified compound with a content of 0.15-3.50 wt %, the modified compound is an organic compound, a weight ratio of the nano-silica gel to the modified compound is 620:1 to 3.5:1; and water with a formula of H₂O and a content of 7.5-86.8 wt %; the nano-silica gel, the modified compound and the water are stirred and mixed at a temperature of 40-80° C. to prepare the modified nano-silica gel.

In one embodiment of the modified nano-silica gel, preferably, based on a total weight of the modified nano-silica gel, the modified nano-silica gel further comprises a basic compound with a content of 0-1 wt %, the basic compound can be added directly or dissolved in water and then added to a mixture comprising a nano-silica gel, a modified compound and water; the basic compound is selected from sodium hydroxide, potassium hydroxide, magnesium hydroxide or calcium hydroxide; the nano-silica gel, the modified compound and the water are stirred and mixed at a temperature of 40-80° C. to form a mixture, and the basic compound is added to the mixture and stirred at a temperature of 40-80° C. to prepare the modified nano-silica gel.

A second object of the invention is to provide a method for preparing a modified nano-silica gel, wherein steps of the preparation method comprise:

material selection step S1: based on a total weight of the modified nano-silica gel, providing 13.0-92.3 wt % of a nano-silica gel, 0.15-3.50 wt % of a modified compound, and 7.5-86.8 wt % of water; wherein the modified compound is an organic compound, a weight ratio of the nano-silica gel to the modified compound is 620:1 to 3.5:1; and mixing step S2: after heating the nano-silica gel to 40-80° C., adding the modified compound, and stirring at the temperature of 40-80° C. thoroughly to prepare the modified nano-silica gel.

In one embodiment of the preparation method, preferably, based on a total weight of the modified nano-silica gel, the material selection step S1 further comprises providing 0-1 wt % of a basic compound; the basic compound is selected from sodium hydroxide, potassium hydroxide, magnesium hydroxide or calcium hydroxide, the basic compound can be added directly or dissolved in water and then added to a mixture comprising a nano-silica gel, a modified compound and water; in the mixing step S2, stirring and mixing the nano-silica gel, the modified compound and the water at a temperature of 40-80° C. to form a mixture, and adding the basic compound to the mixture and stirring at a temperature of 40-80° C. to prepare the modified nano-silica gel.

In one embodiment of the modified nano-silica gel and the preparation method thereof, preferably, the modified compound is selected from acid compounds containing 8 to 18 carbons, alcohol compounds containing 8 to 18 carbons, or ester compounds containing 8 to 18 carbons. More preferably, when the modified compound is an acid compound containing 8 to 18 carbons, the modified compound is selected from n-octanoic acid, n-decanoic acid, lauric acid, or palmitic acid; when the modified compound is an alcohol compound containing 8 to 18 carbons, the modified compound is selected from n-octyl alcohol, n-decyl alcohol, lauryl alcohol, or palmityl alcohol; when the modified compound is an ester compound containing 8 to 18 carbons, the modified compound is selected from glyceryl monocaprylate, glyceryl monocaprate, or monolaurin.

A third object of the invention is to provide a use of a modified nano-silica gel for improving symptoms caused by bacteria. Wherein, the bacteria are selected from one of gram-positive bacteria, gram-negative bacteria and combinations thereof. More specifically, the bacteria are selected from one of *Streptococcus*, *Staphylococcus aureus*, drug-resistant *Staphylococcus aureus*, *Serpulina hyodysenteriae*, *Escherichia coli*, *Salmonella*, *Vibrio vulnificus* and combinations thereof.

A fourth object of the invention is to provide a use of a modified nano-silica gel for improving symptoms caused by viruses. Wherein, the viruses are selected from one of coronavirus, avian influenza virus, novel influenza virus, orthomyxoviridae, paramyxoviridae and combinations thereof.

Regarding the techniques, means and other efficacies adopted by the invention to achieve the above-mentioned objects, preferred and feasible embodiments are described in detail in conjunction with the drawings as follows.

DETAILED DESCRIPTION OF THE INVENTION

In order to facilitate the examiner's understanding of the technical features, content and advantages of the invention and the efficacies it can achieve, the invention will be described in detail as follows in the form of embodiments and with reference to the accompanying drawings. The drawings used herein are merely for the purpose of illustration and supplement for the invention, and may not be the true proportions and precise configurations after the implementation of the invention. Therefore, relationships between the proportions and configurations of the attached drawings should not be used to interpret or limit the scope of the claims in the actual implementation.

The following embodiment 1 to embodiment 2 are the composition ratios and preparation process of a modified nano-silica gel of the invention. An embodiment 3 is a specific embodiment of the modified nano-silica gel with different composition ratios of the invention. An embodiment 4 is an in vivo test of the modified nano-silica gel of the invention applied to pigs.

Embodiment 1: The Composition Ratios of the Modified Nano-Silica Gel of the Invention The compositions of the modified nano-silica gel of the invention comprise a modified nano-silica gel, a modified compound, and water; based on a total weight of the modified nano-silica gel, the modified nano-silica gel comprises 13.0-92.3 wt % of a nano-silica gel, 0.15-3.50 wt % of a modified compound, and 7.5-86.8 wt % of water. In addition, in order to improve a solubility of the modified compound in the water, based on the total weight of the modified nano-silica gel, the modified nano-silica gel can be optionally added with 0-1 wt % of a basic compound.

In this embodiment, the nano-silica gel is a commercially available product provided by Hou Chi Chemical Co., Ltd.; more specifically, a preparation process and a preparation method of the nano-silica gel can be referred to the technical solutions disclosed in Taiwan Invention Patent "nano-silica gel and antibacterial and antiviral applications thereof" of Publication No. 1701216, but the nano-silica gel used in the invention is not limited to the preparation process and the preparation method disclosed in this patent documents, that is, the disclosure of this patent documents is not used to limit a preparation process and a preparation method of the modified nano-silica gel of the invention.

In this embodiment, the modified compound can be selected from acid compounds containing 8 to 18 carbons, alcohol compounds containing 8 to 18 carbons, or ester compounds containing 8 to 18 carbons. Specifically, when the modified compound is an acid compound containing 8 to 18 carbons, the modified compound is preferably selected from n-octanoic acid, n-decanoic acid, lauric acid, or palmitic acid; when the modified compound is an alcohol compound containing 8 to 18 carbons, the modified compound is preferably selected from n-octyl alcohol, n-decyl alcohol, lauryl alcohol, or palmityl alcohol; when the modified compound is an ester compound containing 8 to 18 carbons, the modified compound is preferably selected from glyceryl monocaprylate, glyceryl monocaprate, or monolaurin. More preferably, the modified compound is selected from n-octanoic acid, lauric acid, palmitic acid, n-decyl alcohol, lauryl alcohol, or glycerol monolaurate.

In this embodiment, the formula of the water is $H_2O$.

In this embodiment, the basic compound can be added directly or dissolved in water to make a lye and then added to a mixture comprising a nano-silica gel, a modified compound and water. Preferably, the basic compound is selected from sodium hydroxide, potassium hydroxide, magnesium hydroxide or calcium hydroxide, but is not limited to the foregoing, and can also be selected from common basic compounds in other feed additives. The lye is a sodium hydroxide aqueous solution, a potassium hydroxide aqueous solution, a magnesium hydroxide aqueous solution or a calcium hydroxide aqueous solution.

Embodiment 2: The Preparation Process of the Modified Nano-Silica Gel of the Invention The preparation process of the modified nano-silica gel of the invention comprises: based on the composition ratios of the modified nano-silica gel of embodiment 1, providing a nano-silica gel, a modified compound, and water, and an optional basic compound; then, heating the nano-silica gel to 40-80° C., adding the modified compound to the nano-silica gel, and stirring at a temperature of 40-80° C. thoroughly to prepare a mixture; if a solubility of the modified compound in the water is not good, in order to improve the solubility of the modified compound in the water, dissolving the basic compound in water to prepare a lye, and then adding the lye to the mixture, or directly adding the basic compound to the mixture and stirring at 40-80° C. thoroughly to obtain the modified nano-silica gel.

In this embodiment, heating the nano-silica gel to a fixed temperature between 40-80° C., adding the modified compound to the nano-silica gel at the fixed temperature, and adding the lye to the mixture at the fixed temperature.

In this embodiment, after adding the modified compound to the nano-silica gel, stirring for 1.5-2.5 hours to mix thoroughly, preferably for 2 hours, after adding the basic compound to the mixture, and stirring for 15 to 45 minutes to mix thoroughly, preferably stirring for 30 minutes.

Embodiment 3: Including Embodiments (LP1 to LP18) of the Specific Composition Ratios of the Modified Nano-Silica Gel of the Invention In this embodiment, the nano-silica gel is a commercially available product provided by Hou Chi Chemical Co., Ltd.

In this embodiment, the modified compound is selected from n-octanoic acid (provided by Acros Organics), lauric acid (provided by Keeneyes Industrial Corp.), palmitic acid (provided by Keeneyes Industrial Corp.), n-decyl alcohol (provided by Nantong Reform Chemical Co., Ltd.), lauryl alcohol (provided by Acros Organics), or glycerol monolaurate (provided by Echo Chemical Co., Ltd.). 2 A weight ratio of the nano-silica gel to the modified compound is 620:1 to 3.5:1.

In this embodiment, a preparation temperature of the modified nano-silica gel is selected from 40, 50, 60, 70, or 80° C.

In this embodiment, the basic compound is sodium hydroxide, which can be added directly or dissolved in water to form an alkaline aqueous solution and then added to the mixture comprising the nano-silica gel, the modified compound, and the water. Wherein, the embodiments LP1 to LP9 are embodiments of the modified nano-silica gel with addition of the basic compound, and the embodiments LP10 to LP18 are embodiments of the modified nano-silica gel without addition of the basic compound.

Please refer to Table 1 below for illustration of the specific composition ratios and the preparation process and the preparation method of the embodiments LP1 to LP18.

TABLE 1

| Embodiment | nano-silica gel (g) | Modified compound | (g) | Water (g) | Basic compound (g) | Water 2 (g) | Preparation temperature (° C.) | pH value |
|---|---|---|---|---|---|---|---|---|
| LP1 | 50 | n-octanoic | 2.5 | 22.5 | 0.7 | 6.3 | 70 | 9.7 |
| LP2 | 50 | acid | 1.75 | 15.75 | 0.49 | 4.37 | 70 | 10.2 |
| LP3 | 50 |  | 0.5 | 4.5 | 0.14 | 1.25 | 60 | 10.88 |
| LP4 | 50 | lauric | 2.5 | 22.5 | 0.5 | 4.5 | 80 | 10.59 |
| LP5 | 50 | acid | 1.75 | 15.75 | 0.35 | 3.15 | 80 | 10.69 |
| LP6 | 50 |  | 0.5 | 4.5 | 0.1 | 0.9 | 70 | 11.03 |
| LP7 | 10 | palmitic | 0.5 | 64.52 | 0.08 | 0.72 | 80 | 10.65 |
| LP8 | 10 | acid | 0.35 | 57.15 | 0.05 | 0.49 | 80 | 10.71 |
| LP9 | 10 |  | 0.1 | 44.9 | 0.02 | 0.18 | 80 | 11.07 |
| LP10 | 50 | n-decyl | 2.5 | 22.5 | — | — | 60 | 10.78 |
| LP11 | 50 | alcohol | 1.75 | 15.75 | — | — | 50 | 10.85 |
| LP12 | 50 |  | 0.5 | 4.5 | — | — | 40 | 10.99 |
| LP13 | 50 | lauryl | 2.5 | 22.5 | — | — | 60 | 10.76 |
| LP14 | 50 | alcohol | 1.75 | 15.75 | — | — | 50 | 10.91 |
| LP15 | 50 |  | 0.5 | 4.5 | — | — | 40 | 11.05 |
| LP16 | 50 | monolaurin | 2.5 | 22.5 | — | — | 80 | 10.85 |
| LP17 | 50 |  | 1.75 | 15.75 | — | — | 80 | 10.9 |
| LP18 | 50 |  | 0.5 | 4.5 | — | — | 80 | 11.06 |

Embodiment LP1: preparation of the modified nano-silica gel (LP1) using n-octanoic acid.

Heating 50 g of the nano-silica gel with 10% solid content to 70° C., at this time, adding 2.5 g of n-octanoic acid and 22.5 g of the water to the nano-silica gel, and stirring at 70° C. for 2 hours to obtain the mixture; in addition, dissolving 0.7 g of sodium hydroxide in 6.3 g of the water to obtain an aqueous solution of sodium hydroxide; and then adding the sodium hydroxide aqueous solution to the mixture and stirring at 70° C. for 0.5 hours to obtain the modified nano-silica gel (LP1), pH=9.7.

Embodiment LP2: Preparation of the Modified Nano-Silica Gel (LP2) Using n-Octanoic Acid Heating 50 g of the nano-silica gel with 10% solid content to 70° C., at this time, adding 1.75 g of n-octanoic acid and 15.75 g of the water to the nano-silica gel, and stirring at 70° C. for 2 hours to obtain the mixture; in addition, dissolving 0.49 g of sodium hydroxide in 4.37 g of the water to obtain an aqueous solution of sodium hydroxide; and then adding the sodium hydroxide aqueous solution to the mixture 2 and stirring at 70° C. for 0.5 hours to obtain the modified nano-silica gel (LP2), pH=10.2.

Embodiment LP3: Preparation of the Modified Nano-Silica Gel (LP3) Using n-Octanoic Acid Heating 50 g of the nano-silica gel with 10% solid content to 60° C., at this time, adding 0.5 g of n-octanoic acid and 4.5 g of the water to the nano-silica gel, and stirring at 60° C. for 2 hours to obtain the mixture; in addition, dissolving 0.14 g of sodium hydroxide in 1.25 g of the water to obtain an aqueous solution of sodium hydroxide; and then adding the sodium hydroxide aqueous solution to the mixture and stirring at 60° C. for 0.5 hours to obtain the modified nano-silica gel (LP3), pH=10.88.

Embodiment LP4: Preparation of the Modified Nano-Silica Gel (LP4) Using Lauric Acid Heating 50 g of the nano-silica gel with 10% solid content to 80° C., at this time, adding 2.5 g of lauric acid and 22.5 g of the water to the nano-silica gel, and stirring at 80° C. for 2 hours to obtain the mixture; in addition, dissolving 0.5 g of sodium hydroxide in 4.5 g of the water to obtain an aqueous solution of sodium hydroxide; and then adding the sodium hydroxide aqueous solution to the mixture and stirring at 80° C. for 0.5 hours to obtain the modified nano-silica gel (LP4), pH=10.59.

Embodiment LP5: Preparation of the Modified Nano-Silica Gel (LP5) Using Lauric Acid Heating 50 g of the nano-silica gel with 10% solid content to 80° C., at this time, adding 1.75 g of lauric acid and 15.75 g of the water to the nano-silica gel, and stirring at 80° C. for 2 hours to obtain the mixture; in addition, dissolving 0.35 g of sodium hydroxide in 3.15 g of the water to obtain an aqueous solution of sodium hydroxide; and then adding the sodium hydroxide aqueous solution to the mixture and stirring at 80° C. for 0.5 hours to obtain the modified nano-silica gel (LP5), pH=10.69.

Embodiment LP6: Preparation of the Modified Nano-Silica Gel (LP6) Using Lauric Acid Heating 50 g of the nano-silica gel with 10% solid content to 70° C., at this time, adding 0.5 g of lauric acid and 4.5 g of the water to the nano-silica gel, and stirring at 70° C. for 2 hours to obtain the mixture; in addition, dissolving 0.1 g of sodium hydroxide in 0.9 g of the water to obtain an aqueous solution of sodium hydroxide; and then adding the sodium hydroxide aqueous solution to the mixture and stirring at 70° C. for 0.5 hours to obtain the modified nano-silica gel (LP6), pH=11.03.

Embodiment LP7: Preparation of the Modified Nano-Silica Gel (LP7) Using Palmitic Acid Heating 10 g of the nano-silica gel with 10% solid content to 80° C., at this time, adding 0.5 g of palmitic acid and 64.52 g of the water to the nano-silica gel, and stirring at 80° C. for 2 hours to obtain the mixture; in addition, dissolving 0.08 g of sodium hydroxide in 0.72 g of the water to obtain an aqueous solution of sodium hydroxide; and then adding the sodium hydroxide aqueous solution to the mixture and stirring at 80° C. for 0.5 hours to obtain the modified nano-silica gel (LP7), pH=10.65.

Embodiment LP8: Preparation of the Modified Nano-Silica Gel (LP8) Using Palmitic Acid Heating 10 g of the nano-silica gel with 10% solid content to 80° C., at this time, adding 0.35 g of palmitic acid and 57.15 g of the water to the nano-silica gel, and stirring at 80° C. for 2 hours to obtain the mixture; in addition, dissolving 0.05 g of sodium hydroxide in 0.49 g of the water to obtain an aqueous solution of sodium hydroxide; and then adding the sodium hydroxide aqueous solution to the mixture and stirring at 80° C. for 0.5 hours to obtain the modified nano-silica gel (LP8) with pH=10.71.

Embodiment LP9: Preparation of the Modified Nano-Silica Gel (LP9) Using Palmitic Acid Heating 10 g of the nano-silica gel with 10% solid content to 80° C., at this time, adding 0.1 g of palmitic acid and 44.9 g of the water to the nano-silica gel, and stirring at 80° C. for 2 hours to obtain the mixture; in addition, dissolving 0.02 g of sodium hydroxide in 0.18 g of the water to obtain an aqueous solution of sodium hydroxide; and then adding the sodium hydroxide aqueous solution to the mixture and stirring at 80° C. for 0.5 hours to obtain the modified nano-silica gel (LP9) with pH=11.07.

Embodiment LP10: Preparation of the Modified Nano-Silica Gel (LP10) Using n-Decyl Alcohol Heating 50 g of the nano-silica gel with 10% solid content to 60° C., at this time, adding 2.5 g of n-decyl alcohol and 22.5 g of the water to the nano-silica gel, and stirring at 60° C. for 2 hours to obtain the modified nano-silica gel (LP10), pH=10.78.

Embodiment LP11: Preparation of the Modified Nano-Silica Gel (LP11) Using n-Decyl Alcohol Heating 50 g of the nano-silica gel with 10% solid content to 50° C., at this time, adding 1.75 g of n-decyl alcohol and 15.75 g of the water to the nano-silica gel, and stirring at 50° C. for 2 hours to obtain the modified nano-silica gel (LP11), pH=10.85.

Embodiment LP12: Preparation of the Modified Nano-Silica Gel (LP12) Using n-Decyl Alcohol Heating 50 g of the nano-silica gel with 10% solid content to 40° C., at this time, adding 0.5 g of n-decyl alcohol and 4.5 g of the water to the nano-silica gel, and stirring at 40° C. for 2 hours to obtain the modified nano-silica gel (LP12), pH=10.99.

Embodiment LP13: Preparation of the Modified Nano-Silica Gel (LP13) Using Lauryl Alcohol Heating 50 g of the nano-silica gel with 10% solid content to 60° C., at this time, adding 2.5 g of lauryl alcohol and 22.5 g of the water to the nano-silica gel, and stirring at 60° C. for 2 hours to obtain the modified nano-silica gel (LP13), pH=10.76.

Embodiment LP14: Preparation of the Modified Nano-Silica Gel (LP14) Using Lauryl Alcohol Heating 50 g of the nano-silica gel with 10% solid content to 50° C., at this time, adding 1.75 g of lauryl alcohol and 15.75 g of the water to the nano-silica gel, and stirring at 50° C. for 2 hours to obtain the modified nano-silica gel (LP14), pH=10.91.

Embodiment LP15: Preparation of the Modified Nano-Silica Gel (LP15) Using Lauryl Alcohol Heating 50 g of the nano-silica gel with 10% solid content to 40° C., at this time, adding 0.5 g of lauryl alcohol and 4.5 g of the water to the nano-silica gel, and stirring at 40° C. for 2 hours to obtain the modified nano-silica gel (LP15), pH=11.05.

Embodiment LP16: Preparation of the Modified Nano-Silica Gel (LP16) Using Monolaurin Heating 50 g of the nano-silica gel with 10% solid content to 80° C., at this time, adding 2.5 g of glycerol monolaurate and 22.5 g of the water to the nano-silica gel, and stirring at 80° C. for 2 hours to obtain the modified nano-silica gel (LP16), pH=10.85.

Embodiment LP17: Preparation of the Modified Nano-Silica Gel (LP17) Using Monolaurin Heating 50 g of the nano-silica gel with 10% solid content to 80° C., at this time, adding 1.75 g of glycerol monolaurate and 15.75 g of the water to the nano-silica gel, and stirring at 80° C. for 2 hours to obtain the modified nano-silica gel (LP17), pH=10.9.

Embodiment LP18: Preparation of the Modified Nano-Silica Gel (LP18) Using Monolaurin Heating 50 g of the nano-silica gel with 10% solid content to 80° C., at this time, adding 0.5 g of glycerol monolaurate and 4.5 g of the water to the nano-silica gel, and stirring at 80° C. for 2 hours to obtain the modified nano-silica gel (LP18), pH=11.06.

Embodiment 4: Effects of Using the Modified Nano-Silica Gel of the Invention in Reducing an Amount of Porcine Epidemic Diarrhea (PED) Virus in the Feces of Sows Commercialized product tests are conducted on farms where porcine epidemic diarrhea (hereinafter referred to as PED) broke out in the field to observe whether the sows and piglets are affected by the use of commercial feed additives, and observe changes in the amount of PED virus in the feces through molecular biological testing methods.

Experiment Method

A. Evaluation of Effectiveness in Reducing Toxins Excreted by Sows Before Delivery
1. Experimental Design:

The experiment was carried out in a PED outbreak site in Pingtung County, Taiwan. The PED epidemic has lasted for 3 months. The test lasted for 4 weeks, with sampling once a week, for a total of four samplings. The first sampling was to collect the feces of the sow 4 weeks before farrowing. After the first sampling, DOXVIRE® (2 kg/ton) was added to the sow feed of the whole farm as a control group before the product was used and continued to be added until the test was over. The next three samplings were performed on the same batch of sows, as a test group after the product was used, and the last sampling was 1 week before farrowing. The detailed experimental design and schedule are shown in Table 2.

TABLE 2

| | Experimental design and schedule | | | |
|---|---|---|---|---|
| Sampling | 1st time | 2nd time | 3rd time | 4th time |
| Weeks before delivery (use status) | 4 (before use) | 3 (1 week after use) | 2 (2 weeks after use) | 1 (3 weeks after use) |
| Number of samples | Sampling 20 sows (4 weeks before farrowing), 2 are mixed into 1 sample, a total of 10 samples | Sampling 39 sows (3 weeks before farrowing), 3 are mixed into 1 sample, a total of 13 samples | Sampling 27 sows (2 weeks before farrowing), 3 are mixed into 1 sample, a total of 9 samples | Sampling 42 sows (1 week before farrowing), 3 are mixed into 1 sample, a total of 14 samples |
| Analysis | 1. Average values and scatter diagram of amount of PEDV nucleic acid | 1. Average values and scatter diagram of amount of PEDV nucleic acid | 1. Average values and scatter diagram of amount of PEDV nucleic acid | 1. Average values and scatter diagram of amount of PEDV nucleic acid |

TABLE 2-continued

Experimental design and schedule

| Sampling | 1st time | 2nd time | 3rd time | 4th time |
|---|---|---|---|---|
| | 2. Number of suckling pig deaths during the week | 2. Statistical analysis of difference between amount of viral nucleic acid in this sampling and amount of viral nucleic acid in the first sampling<br>3. Number of suckling pig deaths during the week | 2. Number of suckling pig deaths during the week | 2. Statistical analysis of difference between amount of viral nucleic acid in this sampling and amount of viral nucleic acid in the first sampling<br>3. Number of suckling pig deaths during the week |

2. Sampling:

The sampling method is to use a sterile cotton swab to dip the fresh feces from the sow pens and place it into a sterilized 10 mL centrifuge tube. The sampling quantity and mixing method at each sampling time are shown in Table 2. Mix the sterile cotton swab in a microcentrifuge tube containing 1 mL of 1× phosphate buffered saline (PBS), and store the microcentrifuge tube mixed with the feces in an environment of −80° C., ready for subsequent nucleic acid extraction.

3. Nucleic Acid Extraction:

Use the commercial Taco™ DNA/RNA Extraction Kit to extract nucleic acid, and follow the instructions provided.

4. Real-Time Quantitative Polymerase Chain Reaction:

The extracted nucleic acid is used in the commercial kit GeneReach Biotechnology® IQ real PEDV simplex quantitative system to perform PEDV real-time quantitative polymerase chain reaction (qPCR). Each action unit contains 20 μL PreMix Buffer, 2 μL IQzyme DNA polymerase, 1 μL reverse transcriptase and 1 μL nucleic acid sample. Use the positive control group provided by the commercial kit and dilute ten times (10-fold dilution, 1:10 dilution) for five times consecutively to establish a standard curve. The reaction solution is placed in the Applied Biosystems™ StepOnePlus for real-time quantitative polymerase chain reaction, and the reaction conditions are set as follows: 42° C./30 minutes, and 40 cycles at 95° C./15 seconds and 60° C./60 seconds.

5. Statistical Analysis

Take the logarithm (Log 10) of the nucleic acid amount and the average value of the sow fecal virus in 4 sampling times, and make a scatter diagram, and finally use the statistical analysis software IBM SPSS Statistics, and use the Mann-whitney test statistical method to evaluate the difference in the amount of viral nucleic acid before and 1 week and 3 weeks after using the modified nano-silica gel of the invention. If the P value is less than 0.05, it is determined that there is a significant difference between the two, as shown in Table 2.

B. Evaluation of Slowing Down the Death of Piglets

1. Experimental Design:

After sampling the sows of test A, the modified nano-silica gel of the invention is added to the sow feed of the whole farm. Collect the number of suckling piglet deaths in each week during the test period (4 weeks) and make a line graph to evaluate the deaths of suckling piglets before using the product, and 1 week, 2 weeks and 3 weeks after using the product.

A. Effect of Effectiveness in Reducing Toxins Excreted by Sows Before Delivery

Figure 1:
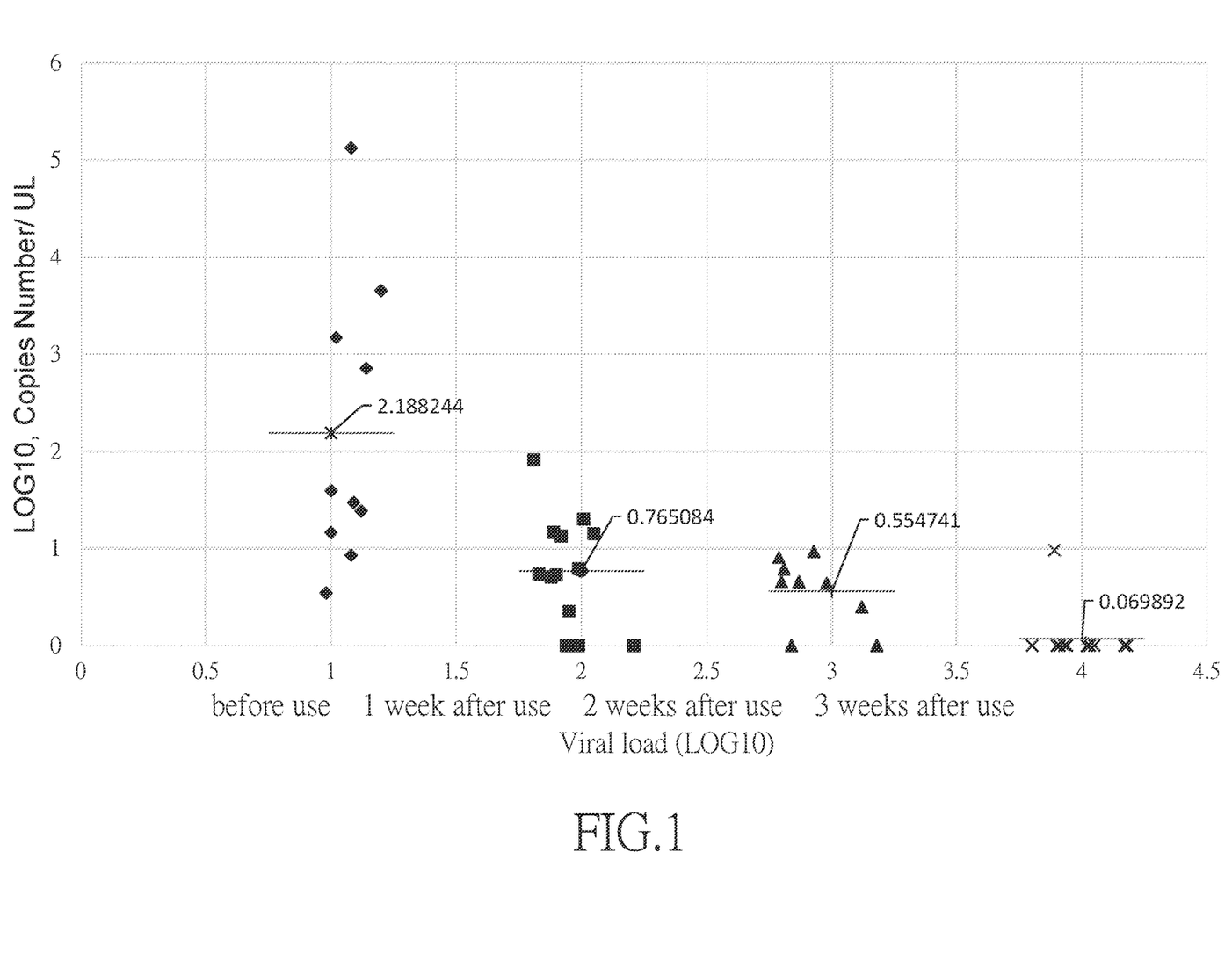
FIG. 1 is a scatter diagram and average values of logarithm of sow fecal virus amounts before delivery in an embodiment 4.

The average values and positive rates of the sow fecal virus amount of each sample in each week before delivery are shown in Table 3, and the logarithmic scatter diagram and the average values are shown in FIG. 1. Table 4 shows the statistical correlation and p value of the amount of viral nucleic acid before using the modified nano-silica gel of the invention and one week and three weeks after using the modified nano-silica gel of the invention.

TABLE 3

Average values and positive rates of the sow fecal virus amount of each sample in each week before delivery

| | Before use | 1 week after use | 2 weeks after use | 3 weeks after use |
|---|---|---|---|---|
| Average viral load (copies/uL) | 14,006.03 | 12.88 | 4.35 | 0.68 |
| Positive rate (Number of Positives/Number of total samples) | 100% (9/9) | 76.92% (10/13) | 77.78% (7/9) | 7.12% (1/14) |

TABLE 4

Scatter diagram and average values of logarithm of sow fecal virus amount before delivery

| | Before and 1 week after using the modified nano-silica gel | Before and 3 weeks after using the modified nano-silica gel |
|---|---|---|
| Significant difference (p value) | Significant difference (p = 0.04) | Significant difference (p < 0.01) |

B. Effect of Slowing Down the Death of Piglets

Figure 2:
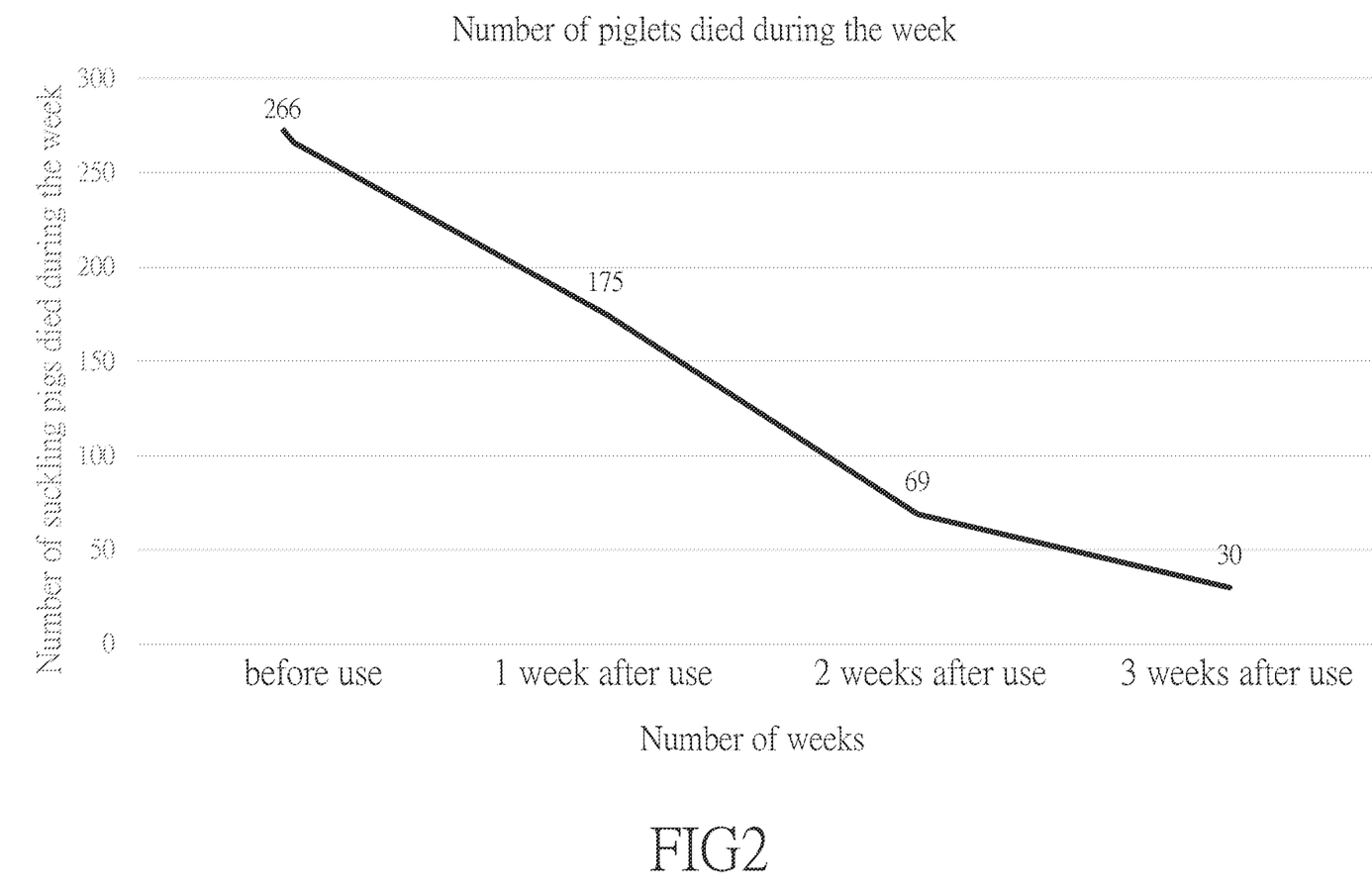
FIG. 2 is a broken line graph of a number of suckling piglet deaths in each week in the embodiment 4.

The broken line graph of the number of suckling pig deaths in each week during the test period is shown in FIG. 2.

From the above experimental results of this embodiment, it can be known that fecal-oral transmission is the main transmission mode of PEDV. In the control of PED, in addition to stricter biosecurity measures and immunization of sows to provide adequate protection for piglets, reducing amount of toxins excreted by sows is also an important part. If a sow is naturally infected with PEDV in a sow barn or farrowing barn, or is actively infected when immunized, the sow will have the opportunity to detoxify through feces and transmit the pathogen to the piglets, causing infection and death of the piglets. According to documents, after the first PEDV vaccination of sows after delivery and new sows, excreting of toxins can be detected 3 days the soonest after vaccination, and excreting of toxins can be as long as 2 weeks.

In this test, in the sow feces before adding the modified nano-silica gel of the invention, all the mixed samples are PEDV positive (9/9), the average virus amount is 14,006 copies/uL, and the highest viral load could reach 133,223 copies/uL; and 1 week after use, the positive rate of the PED test of the mixed sample is 76.92% (10/13), the average viral load is reduced to 12.9 copies/uL, and the logarithmic value of the viral load is significantly different from that before use ($p=0.04$) (Table 2), showing that the amount of PEDV excreted by sows from feces is significantly decreased. However, this test did not set up a control group without adding the product to compare the differences between the two. Until 3 weeks after the product is used, only 1 mixed sample is positive (1/14), and the viral load is only 9.5 copies/uL, indicating that most sows have stopped excreting toxins 3 weeks after the product is used.

As for the death of suckling pigs, before the modified nano-silica gel of the invention is used, 266 suckling pigs died during the week, but after the product is used, the death of piglets is gradually reduced. Until 3 weeks after use, only 30 piglets died in the week (FIG. 2), showing that if there are only a few pathogens in the farrowing barn environment and other biosecurity measures are adequate, reducing the amount of toxins excreted by sows can reduce the chance of piglets being infected and thereby reducing piglet deaths.

In summary, the modified nano-silica gel provided by the invention can be antibacterial and antiviral, based on the results of the embodiments, it can be proved that the modified nano-silica gel of the invention has the ability to reduce the viral activity of PED virus. In addition, it has been proved to be effective in reducing the viral load in pig breeding farms in vivo experiments. After the sows are administered with the modified nano-silica gel of the invention four weeks before delivery, the viral load of PED viruses in the fecal samples of the sows decreases.

Although the specific embodiments of the invention are disclosed in the above implementation modes, they are not intended to limit the invention. The specification relating to the above embodiments should be construed as exemplary rather than as limitative of the invention, with many variations and modifications being readily attainable by a person having ordinary skill in the art to which the invention pertains without departing from the principles and spirit thereof as defined by the appended claims and their legal equivalents.

What is claimed is:

1. A method for preparing a modified nano-silica gel, steps of the method comprising:

material selection step S1: based on a total weight of the modified nano-silica gel, providing 13.0-92.3 wt % of a nano-silica gel, 0.15-3.50 wt % of a modified compound, 0.02-1 wt % of a basic compound, and 7.5-86.8 wt % of water; wherein the modified compound is an organic compound, a weight ratio of the nano-silica gel to the modified compound is 620:1 to 3.5:1; wherein the nano-silica gel comprises a silica that is an inorganic clay; wherein the modified compound is selected from n-octanoic acid, n-decanoic acid, lauric acid, palmitic acid, n-octyl alcohol, n-decyl alcohol, lauryl alcohol, palmityl alcohol, glyceryl monocaprylate, glyceryl monocaprate, or monolaurin; and mixing step S2: after heating the nano-silica gel to 40-80° C., adding the modified compound, and stirring at the temperature of 40-80° C. thoroughly to prepare the modified nano-silica gel.

2. The method for preparing the modified nano-silica gel as claimed in claim 1, wherein in the material selection step S1, the basic compound being selected from sodium hydroxide, potassium hydroxide, magnesium hydroxide or calcium hydroxide;

in the mixing step S2, stirring and mixing the nano-silica gel, the modified compound and the water at a temperature of 40-80° C. to form a mixture, and adding the basic compound to the mixture and stirring at a temperature of 40-80° C. to prepare the modified nano-silica gel.

* * * * *